(12) United States Patent
Nakamura et al.

(10) Patent No.: US 7,985,177 B2
(45) Date of Patent: Jul. 26, 2011

(54) ENDOSCOPE FOR MAGNIFIED IMAGE OBSERVATION

(75) Inventors: Tetsuya Nakamura, Saitama (JP); Akira Yamamoto, Tokyo (JP); Yae Kurosawa, Kanagawa (JP); Yusuke Iimori, Tokyo (JP); Pilryon Lee, Kanagawa (JP)

(73) Assignee: Hoya Corporation, Tokyo (JP)

( * ) Notice: Subject to any disclaimer, the term of this patent is extended or adjusted under 35 U.S.C. 154(b) by 911 days.

(21) Appl. No.: 11/567,315

(22) Filed: Dec. 6, 2006

(65) Prior Publication Data

US 2007/0149851 A1 Jun. 28, 2007

(30) Foreign Application Priority Data

Dec. 6, 2005 (JP) ................................ 2005-351954

(51) Int. Cl.
*A61B 1/06* (2006.01)
*A61B 1/00* (2006.01)
*A61B 5/05* (2006.01)
(52) U.S. Cl. ......... 600/175; 600/127; 600/129; 600/414
(58) Field of Classification Search .................. 600/1–5, 600/104, 127, 129, 175, 407, 420, 426, 431–435, 600/458, 414; 604/58, 116; 606/116, 117, 606/1, 186
See application file for complete search history.

(56) References Cited

U.S. PATENT DOCUMENTS

| | | | | |
|---|---|---|---|---|
| 5,569,237 A * | 10/1996 | Beckenstein | ..................... | 606/1 |
| 6,095,970 A * | 8/2000 | Hidaka et al. | ................. | 600/110 |
| 6,524,234 B2 * | 2/2003 | Ouchi | ............................ | 600/127 |
| 2003/0187349 A1 * | 10/2003 | Kaneko et al. | ................ | 600/425 |
| 2004/0030325 A1 * | 2/2004 | Cahir et al. | ....................... | 606/9 |
| 2004/0158129 A1 * | 8/2004 | Okada et al. | ................. | 600/168 |
| 2005/0052753 A1 | 3/2005 | Kanai | | |

FOREIGN PATENT DOCUMENTS

| | | |
|---|---|---|
| JP | 2003-290127 | 10/2003 |
| JP | 2004-344201 | 12/2004 |
| JP | 2005-000640 | 1/2005 |
| JP | 2005-080769 | 3/2005 |

OTHER PUBLICATIONS

English Language Abstract of JP 2004-344201.
English Language Abstract of JP 2005-080769.
English Language Abstract of JP 2005-000640.
English Language Abstract of JP 2003-290127.

* cited by examiner

*Primary Examiner* — Thomas J Sweet
*Assistant Examiner* — Ryan Henderson
(74) *Attorney, Agent, or Firm* — Greenblum & Bernstein P.L.C.

(57) ABSTRACT

An endoscope for magnified image observation configured to observe a magnified image of in vivo tissue comprises an insertion part configured to be inserted into a body, a magnified image observation port configured to take in the magnified image of the in vivo tissue in one of a state where the magnified image observation port is in contact with the in vivo tissue and a state where the magnified image observation port is in proximity to the in vivo tissue, the observation port being provided at a distal end of the insertion part, and a marking unit configured to mark the in vivo tissue in one of the state where the magnified image observation port is in contact with the in vivo tissue and the state where the magnified image observation port is in proximity to the in vivo tissue.

9 Claims, 16 Drawing Sheets

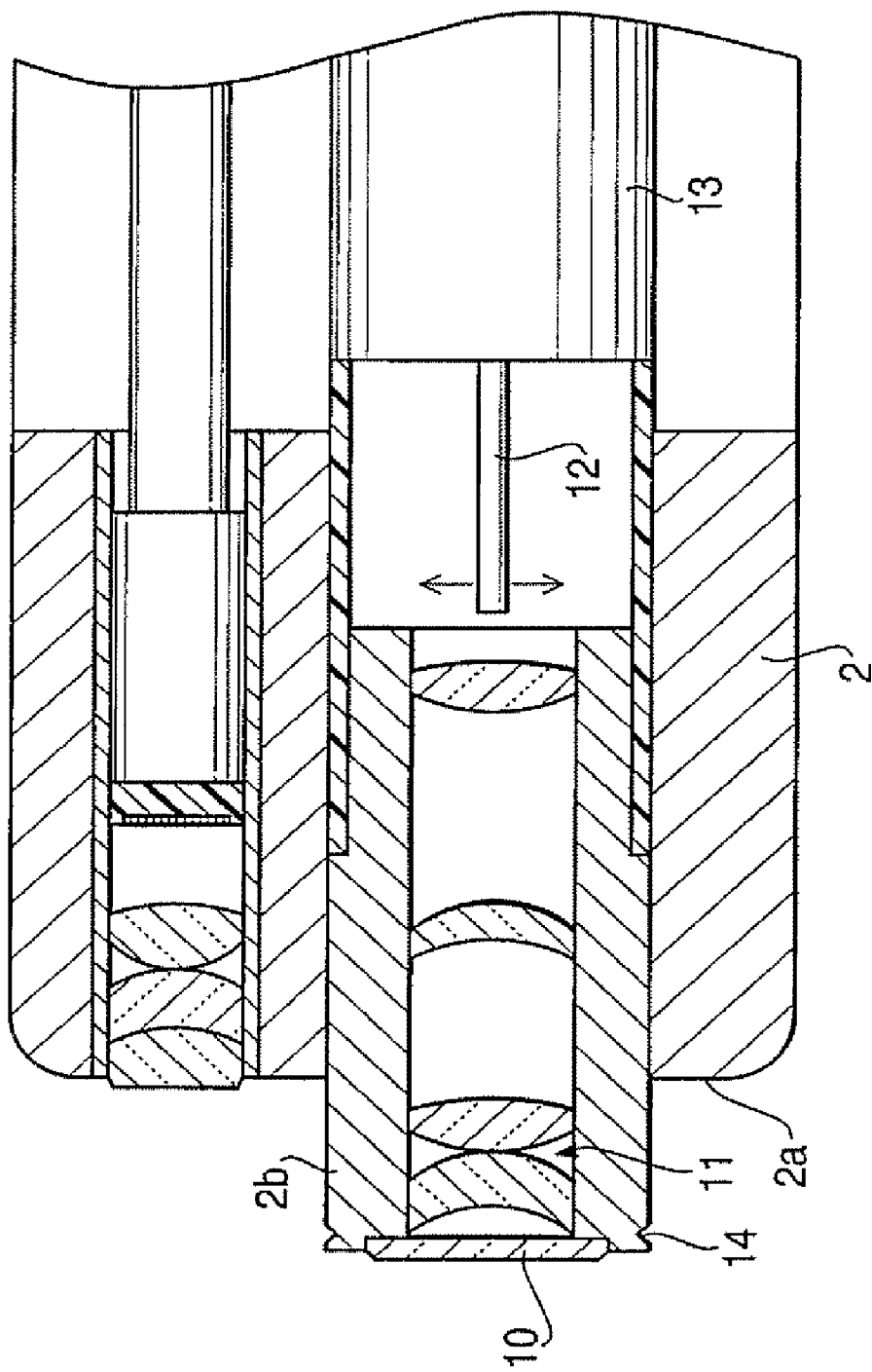
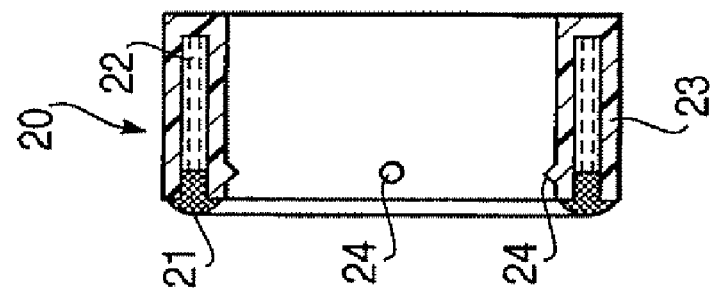
FIG. 3

ENDOSCOPE FOR MAGNIFIED IMAGE OBSERVATION

BACKGROUND OF THE INVENTION

The present invention relates to an endoscope for magnified image observation with an observation port for observing a magnified image being provided at a distal end of an insertion part to take in the magnified image to be observed.

There is widely generally performed a procedure to examine whether lesion or the like exists by visually observing an inside of in vivo hollow viscera with an endoscope. However, even though the lesion can be found with such an endoscope, in many cases, it is difficult to make a definite diagnosis about whether the lesion is cancerous tissue.

Hence, some tissues are taken from the lesion that has been judged that it might be the cancerous tissue by the endoscope inspection with a bioptome and the like. However, in spite of the lesion being concluded not to be the cancerous tissue in most cases, mucous membrane of an in vivo luminal wall is so damaged merely by the tissue examination as to bleed.

For this reason, recently, an endoscope for magnified image observation that is able to microscopically observe a super-magnified image of a region with a diameter less than 1 mm, such as a confocal endoscope, has been developed. Therefore, it has become possible to make a definite diagnosis about whether the lesion is the cancerous tissue only by direct observation with such an endoscope without taking the biopsy tissues. For example, the endoscope of this kind is disclosed in Japanese Patent Provisional Publications No. 2004-344201, No. 2005-80769, and No. 2005-640.

In the meantime, when a cancer cell is found by the examination of an affected area, a medical treatment is required for the affected area. In this case, after the tissues have been taken from the affected area with the bioptome, it is possible to confirm and record a location of a bleeding portion since the location can easily be specified in an observation image by a normal wide-field endoscope.

On the other hand, there can be displayed on a screen only too small region of the observation image microscopically super-magnified by the endoscope for magnified image observation. Therefore, there is caused such a problem that it is impossible to understand to which portion of an internal organ the affected area corresponds, and that even though the cancer cell is found, it is impossible to accurately specify the location thereof.

SUMMARY OF THE INVENTION

The present invention is advantageous in that there can be provided an improved endoscope for magnified image observation that allows a user to easily and accurately specify to which portion in a body a microscopic area observed in an image microscopically super-magnified by the endoscope corresponds.

According to an aspect of the present invention, there is provided an endoscope for magnified image observation configured to observe a magnified image of in vivo tissue, which includes: an insertion part configured to be inserted into a body; a magnified image observation port configured to take in the magnified image of the in vivo tissue in one of a state where the magnified image observation port is in contact with the in vivo tissue and a state where the magnified image observation port is in proximity to the in vivo tissue, the observation port being provided at a distal end of the insertion part; and a marking unit configured to mark the in vivo tissue in one of the state where the magnified image observation port is in contact with the in vivo tissue and the state where the magnified image observation port is in proximity to the in vivo tissue.

Optionally, the marking unit may be configured to mark the in vivo tissue by applying marking liquid to a surface of the in vivo tissue. Optionally, the marking unit may be provided to surround the magnified image observation port.

Optionally, the marking unit may be formed as a ring surrounding the magnified image observation port. Yet optionally, the marking unit may be configured to be detachable from the magnified image observation port.

Still optionally, the endoscope for magnified image observation may further comprise a fixing mechanism for fixing a state where the marking unit is attached to the magnified image observation port so as to surround the magnified image observation port.

Further optionally, the fixing mechanism may be a click member configured to elastically fix the marking unit around the magnified image observation port.

Optionally, the magnified image observation port may be configured to be protruded from a distal end surface of the insertion part. In this case, the marking unit may be formed to have the same length as the protruded length of the magnified image observation port.

Optionally, the marking unit may include a marking liquid applying member provided along an outer edge of the magnified image observation port to apply the marking liquid to the in vivo tissue.

Further optionally, the marking unit may include a marking liquid filled portion configured to be filled with the marking liquid to be supplied to the marking liquid applying member, the marking liquid filled portion being provided adjacent to the marking liquid applying member.

Still optionally, the marking liquid filled portion may be configured such that it is capable of being separated from the marking liquid applying member.

Optionally, the marking liquid filled portion may be integrated with the marking liquid applying member. Optionally, the marking unit may include a marking liquid refilling opening for refilling the marking liquid into the marking liquid filled portion.

Yet optionally, the marking liquid filled portion may be formed in a shape of a cylinder.

Optionally, the endoscope for magnified image observation may further include a front hood configured to be attached around the distal end of the insertion part so as to surround the distal end of the insertion part, the front hood being configured to be detachable from the distal end of the insertion part. In this case, the marking unit may be provided at the front hood.

Optionally, the marking liquid applying member may be formed as one of a contiguous ring and a noncontiguous ring along an outer edge of the magnified image observation port.

Optionally, the marking liquid applying member may be formed as one or more dots arranged along an outer edge of the magnified image observation port with a space between each adjacent couple of the one or more dots.

Optionally, the endoscope for magnified image observation may further include a marking shape control system that allows a user thereof to change a shape of a marking to be provided by the marking unit from a rear anchor side of the insertion part.

Yet optionally, the marking liquid applying member may be formed as a plurality of dots arranged along an outer edge of the magnified image observation port with a space between each adjacent couple of the plurality of dots. In this case, the marking shape control system may be configured to control the number of the dots to be exposed outside among the plurality of dots.

Still optionally, the marking shape control system may be configured to move a sheet arranged to be movable along surfaces of the plurality of dots by a remote operation from the rear anchor side of the insertion part.

Optionally, the endoscope for magnified image observation may further comprise a confocal optical system inside the magnified image observation port.

BRIEF DESCRIPTION OF THE ACCOMPANYING DRAWINGS

FIG. 3 is a cross-sectional side view of the distal end portion of the insertion part of the endoscope for magnified image observation in a state where a marking unit is detached therefrom according to the first embodiment of the present invention.

Figure 7:
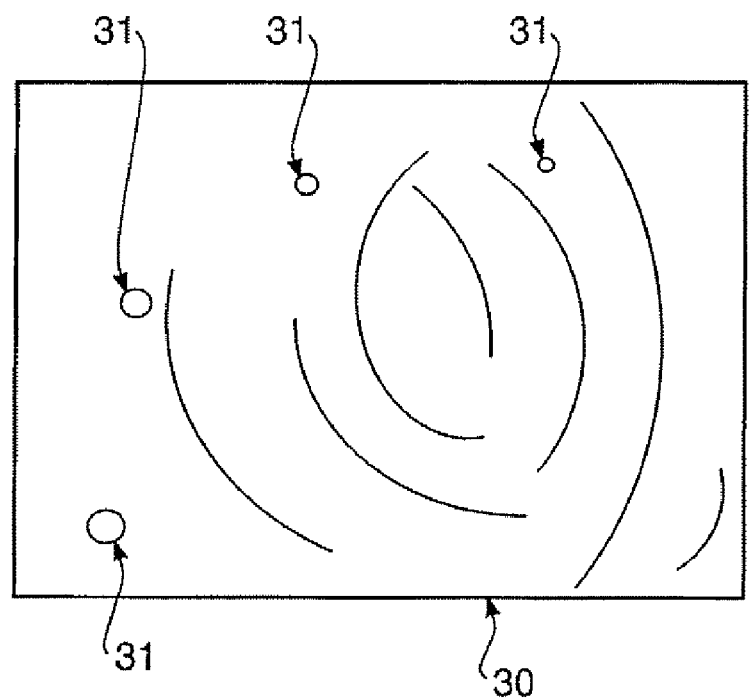

FIG. 7 schematically shows an example of a normal observation image of a marked state according to the first embodiment of the present invention.

Figure 8:
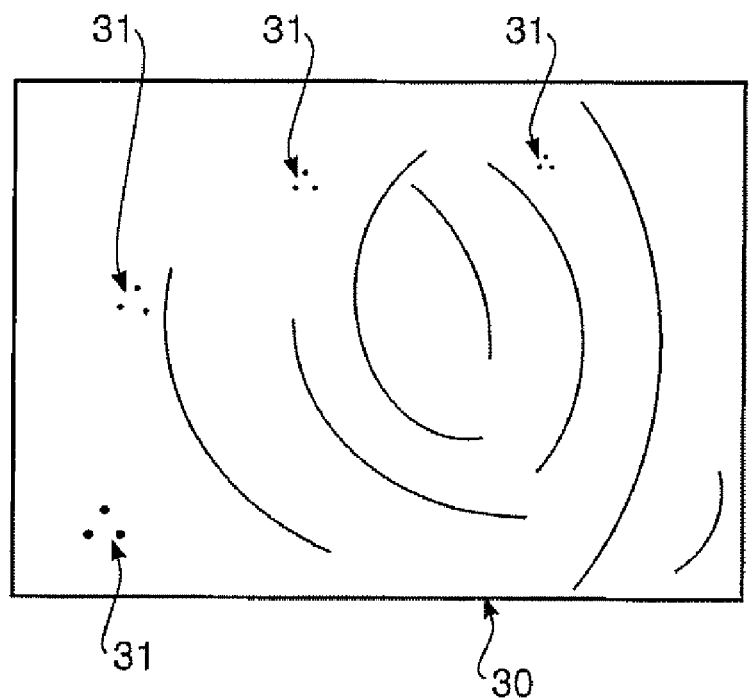

FIG. 8 schematically shows an example of a normal observation image of a marked state according to the third embodiment of the present invention.

Figure 9:
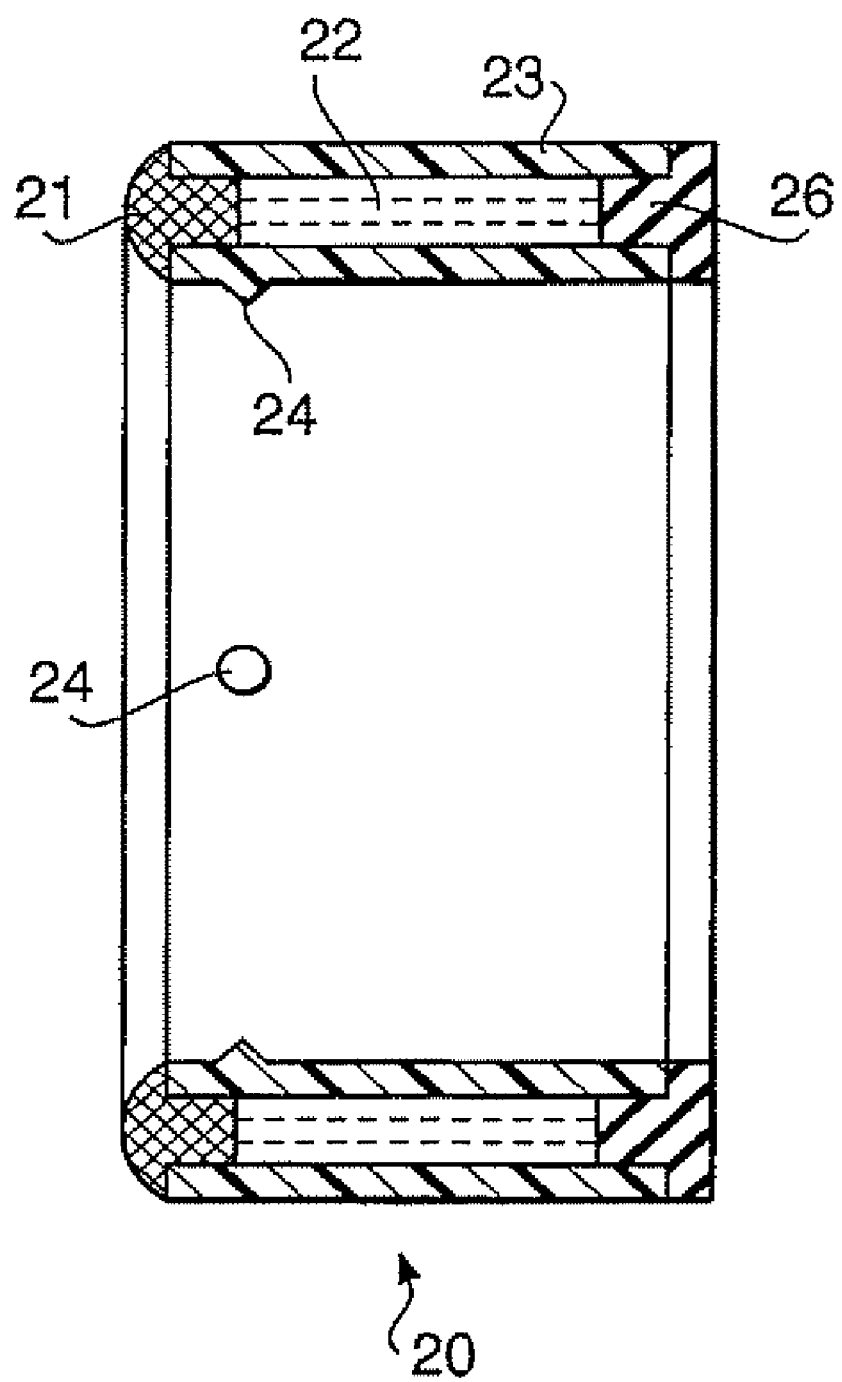

FIG. 9 is a cross-sectional side view of a marking unit of the endoscope for magnified image observation according to a fourth embodiment of the present invention.

Figure 10:
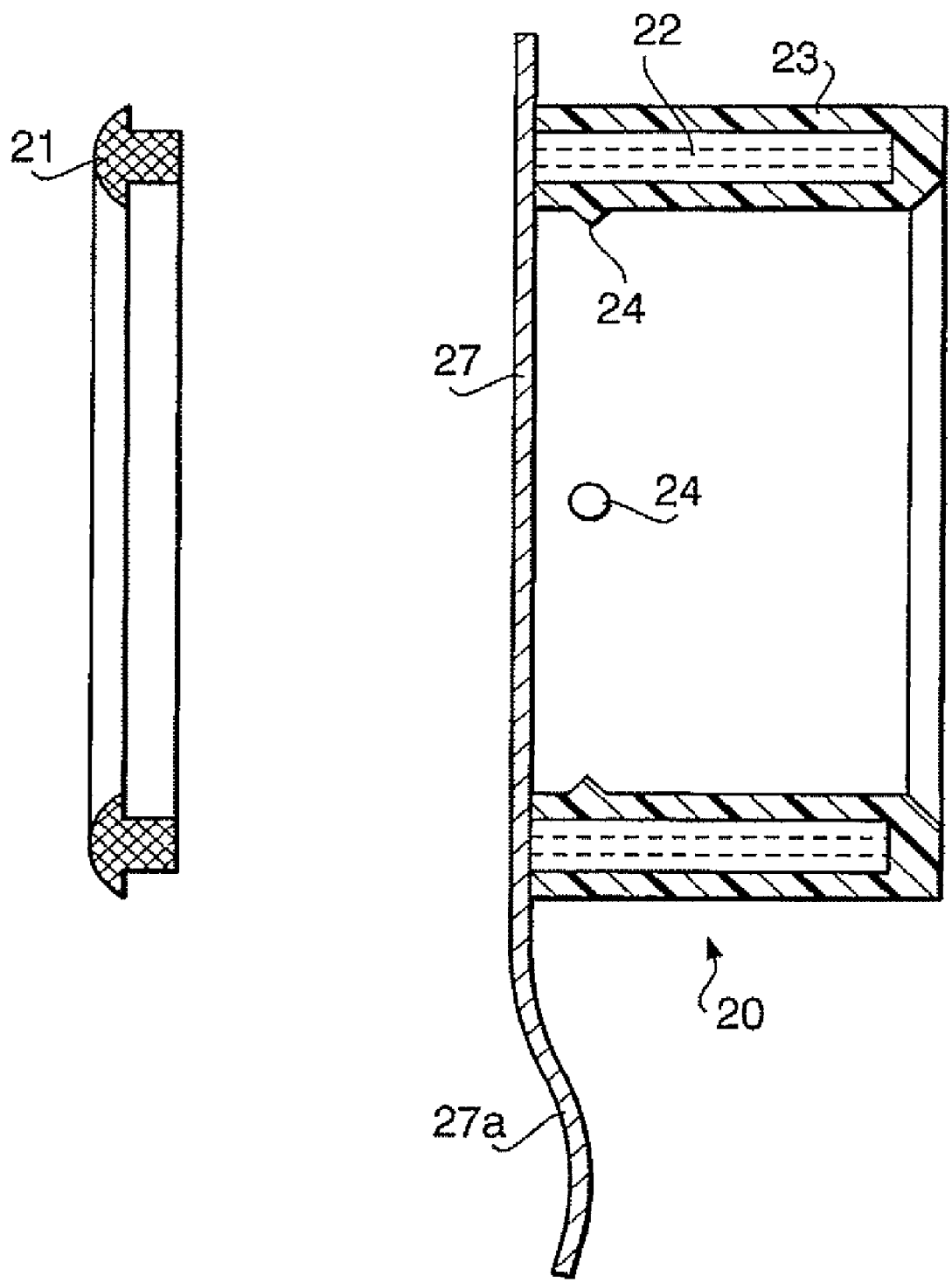

FIG. 10 is a cross-sectional side view of a marking unit of the endoscope for magnified image observation according to a fifth embodiment of the present invention.

Figure 11:
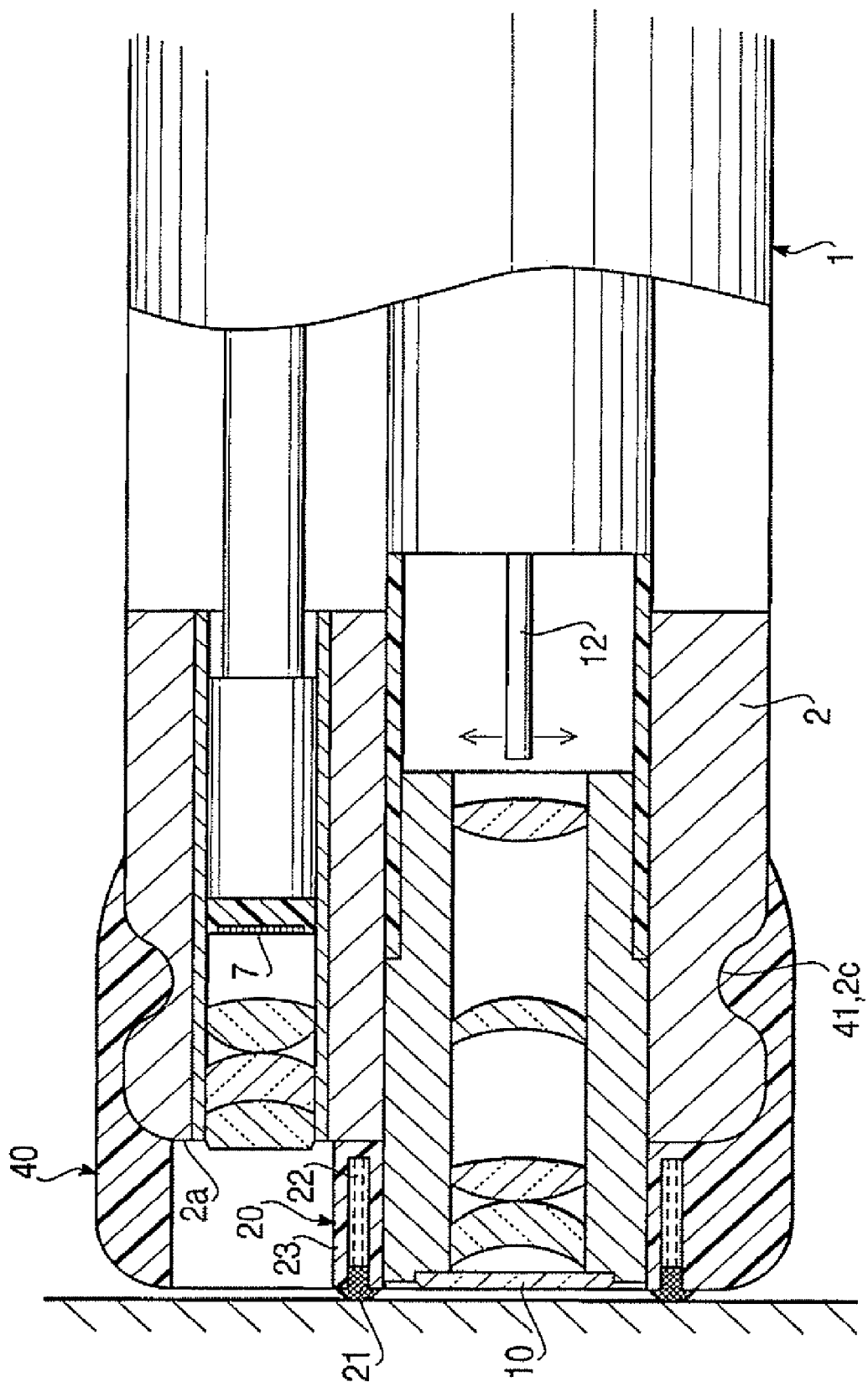

FIG. 11 is a cross-sectional side view of a distal end portion of the insertion part of the endoscope for magnified image observation with a front hood (marking unit) being attached thereto according to a sixth embodiment of the present invention.

Figure 12:
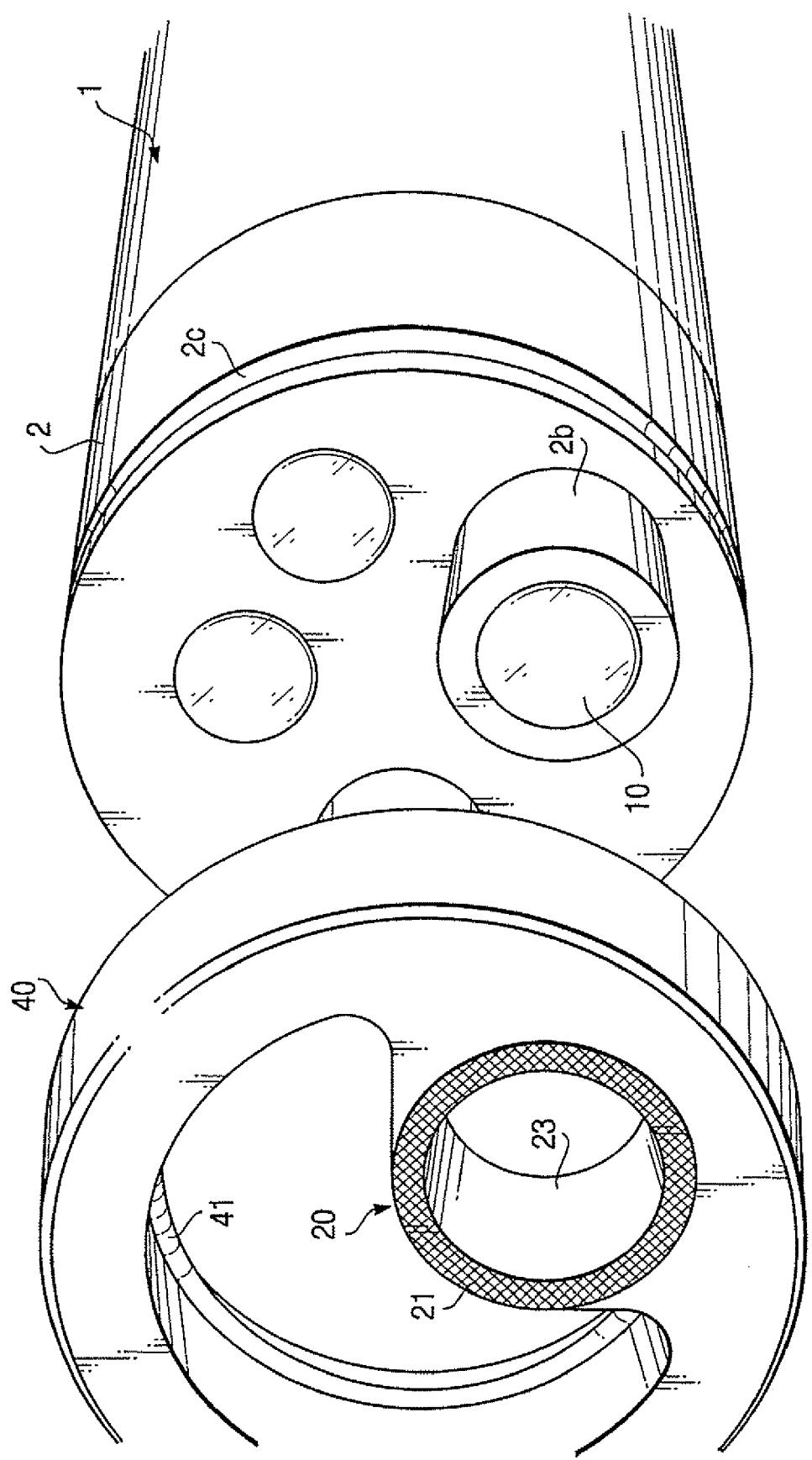

FIG. 12 is a perspective view of the distal end portion of the insertion part of the endoscope for magnified image observation in a state where the front hood (marking unit) is detached therefrom according to the sixth embodiment of the present invention.

Figure 13:
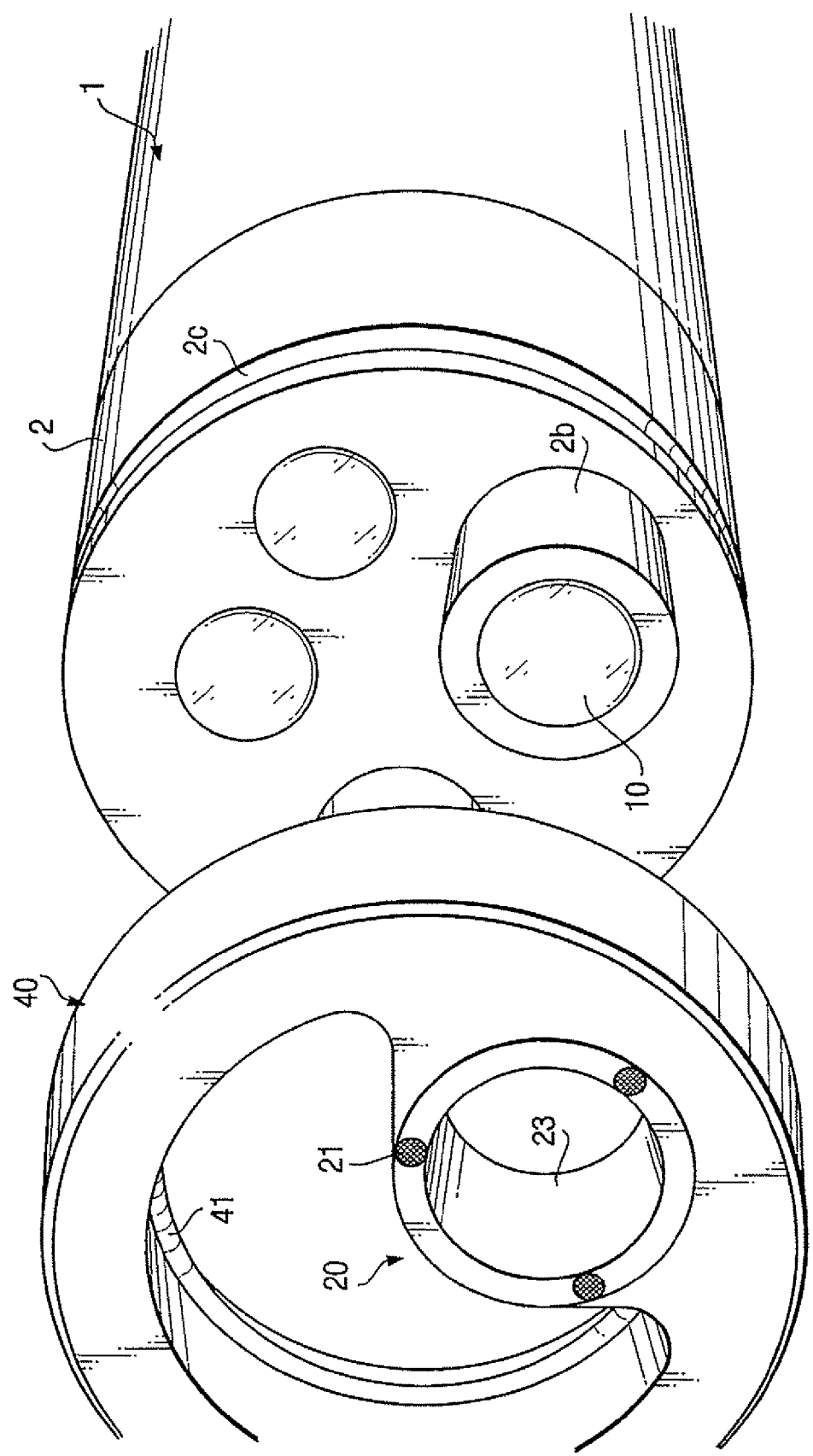

FIG. 13 is a perspective view of the distal end portion of the insertion part of the endoscope for magnified image observation in a state where a front hood (marking unit) is detached therefrom according to a seventh embodiment of the present invention.

Figure 14:
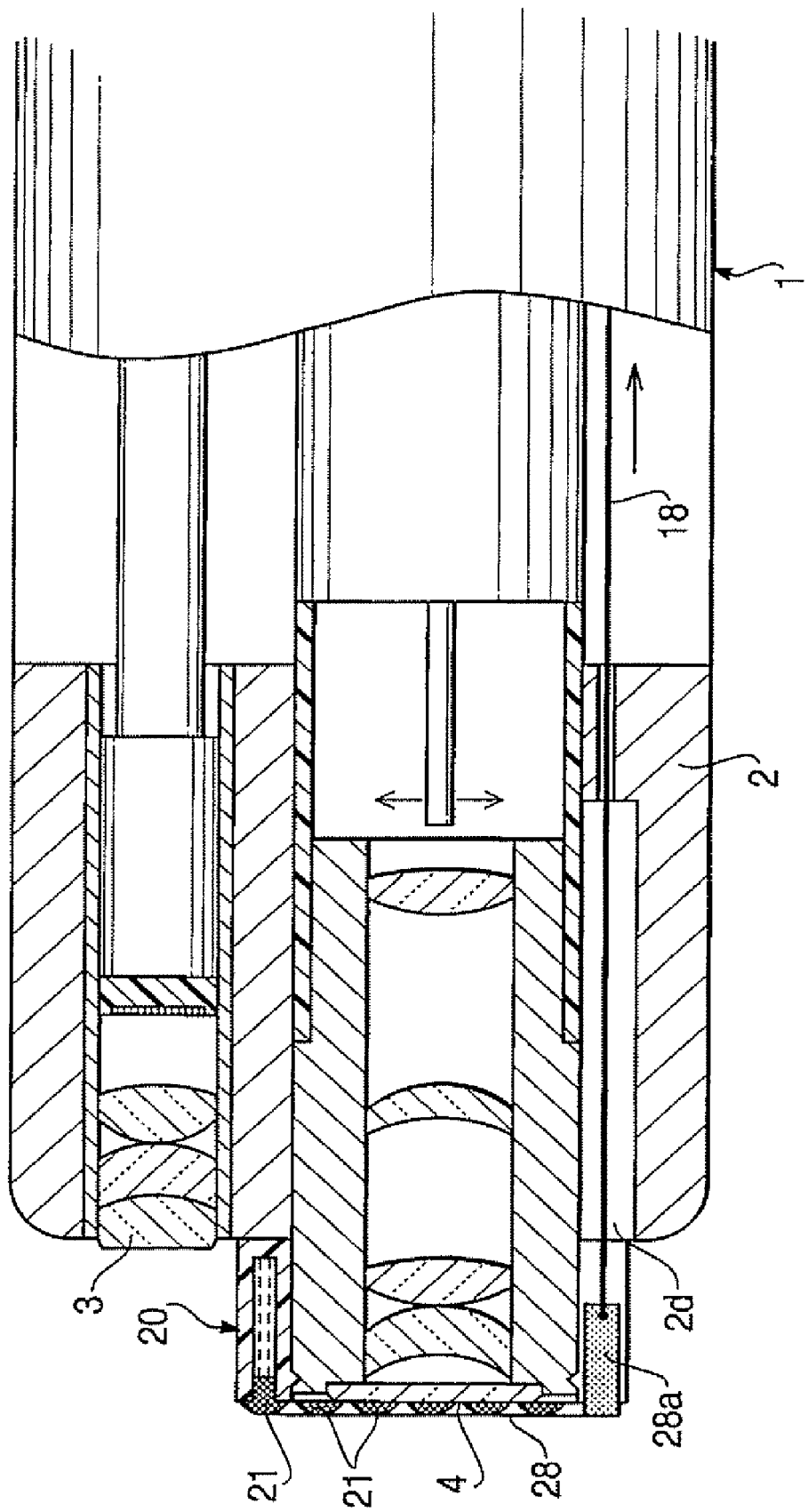

FIG. 14 is a cross-sectional side view of a distal end portion of the insertion part of the endoscope for magnified image observation with a marking unit being attached thereto according to an eighth embodiment of the present invention.

Figure 15:
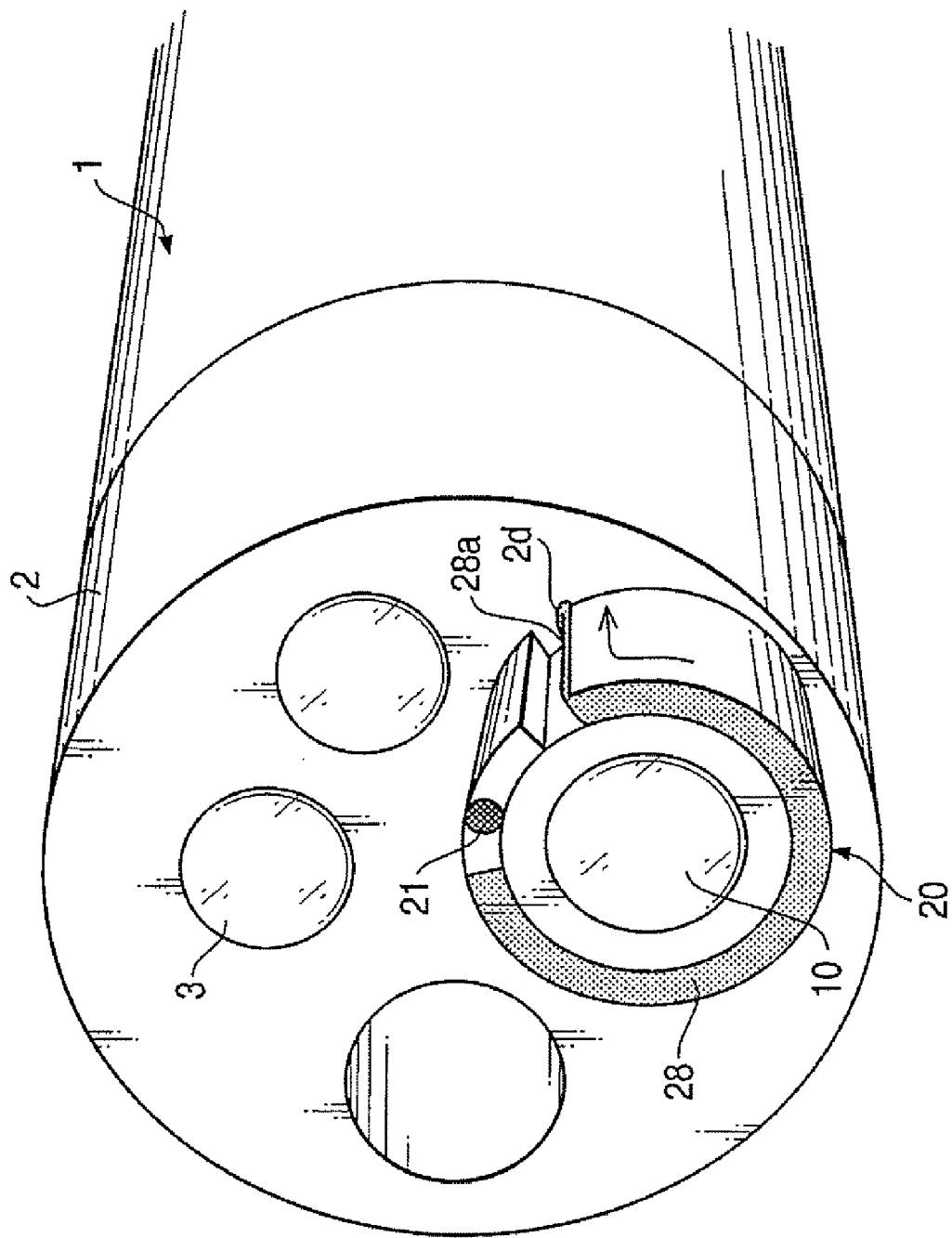

FIG. 15 is a perspective view of the distal end portion of the insertion part of the endoscope for magnified image observation with the marking unit being attached thereto according to the eighth embodiment of the present invention.

Figure 16:
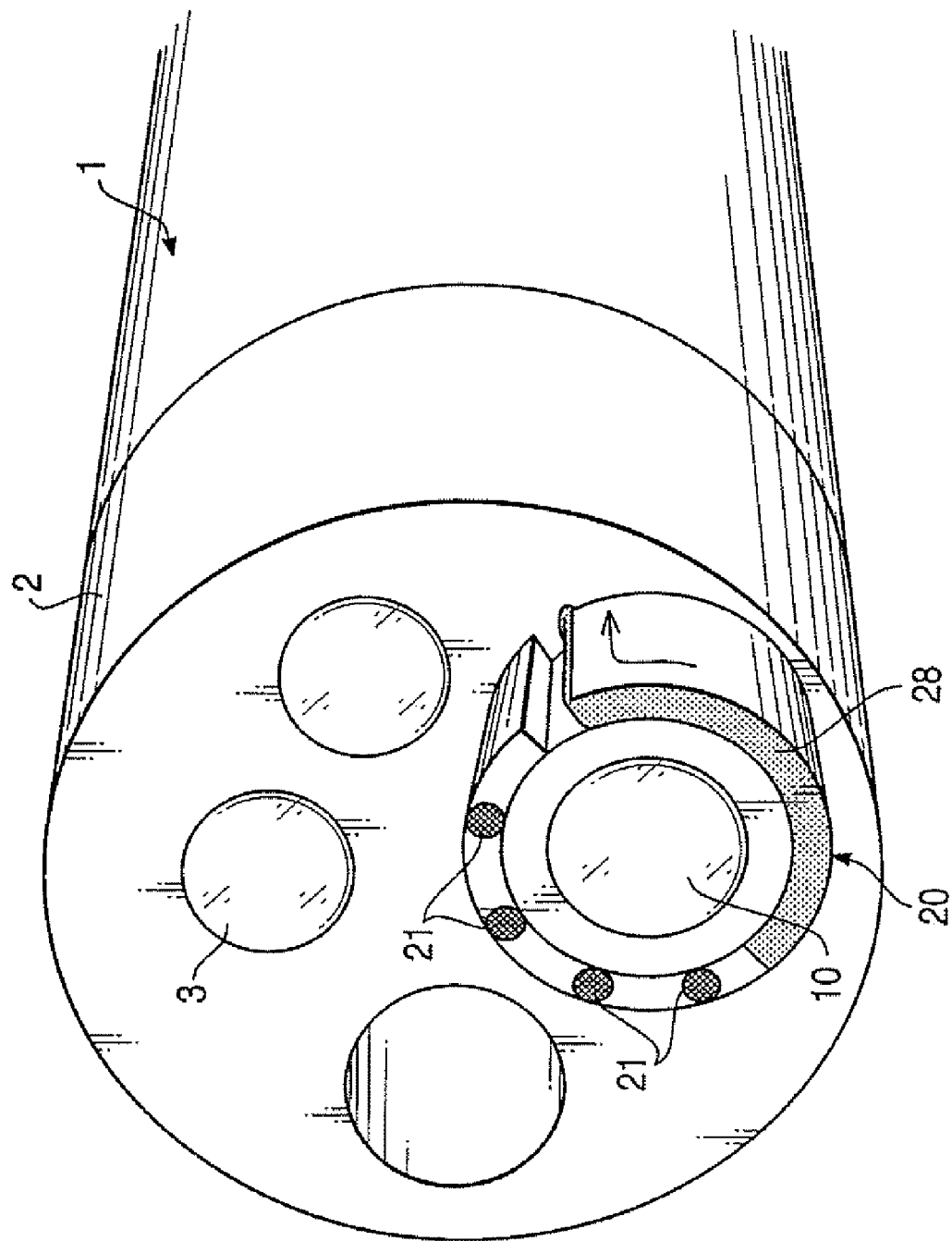

FIG. 16 is a perspective view for illustrating an operation of the distal end portion of the insertion part of the endoscope for magnified image observation according to the eighth embodiment of the present invention.

Figure 17:
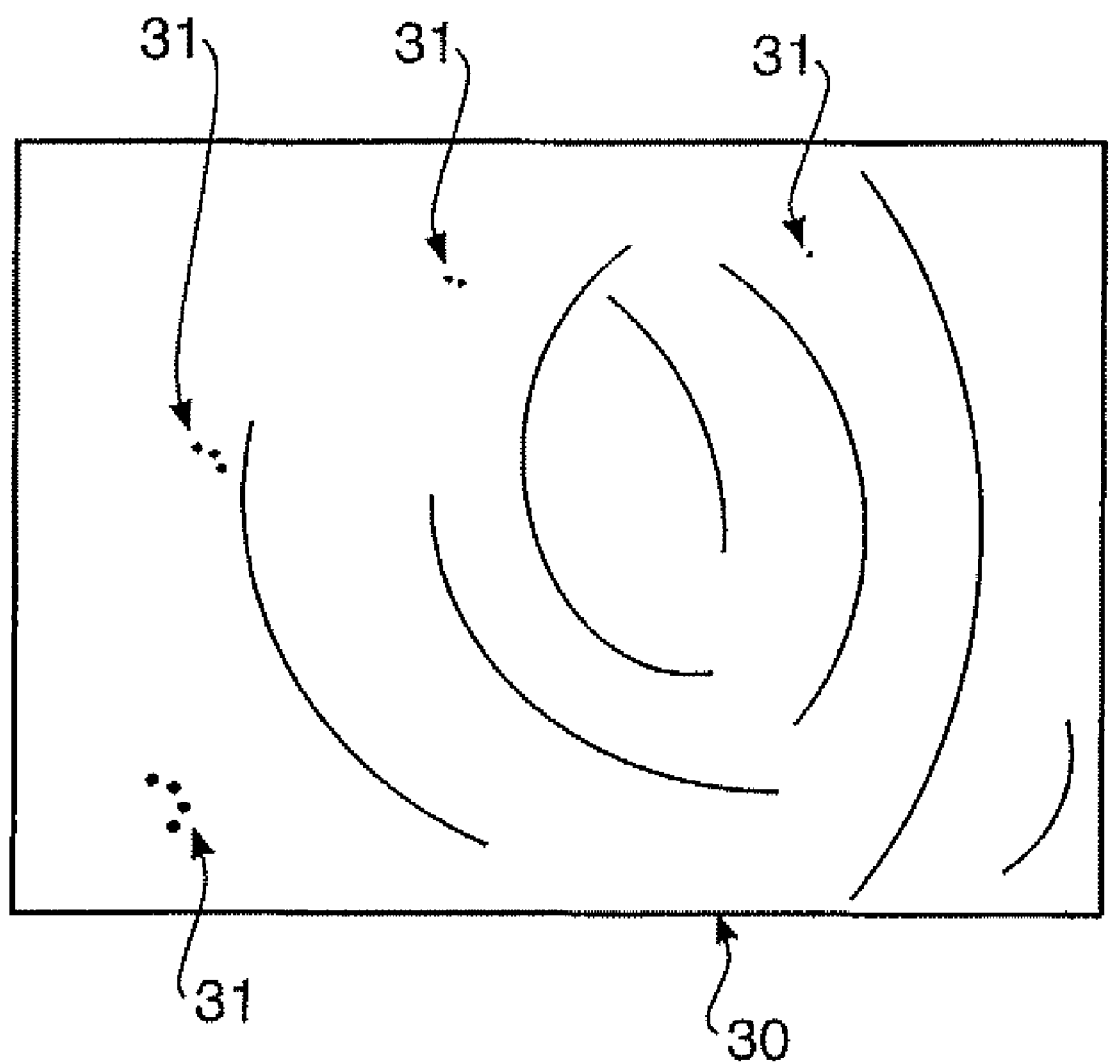

FIG. 17 schematically shows an example of a normal observation image in a marked state according to the eighth embodiment of the present invention.

DETAILED DESCRIPTION OF THE EMBODIMENTS

In an endoscope for magnified image observation having a magnified image observation port at a distal end of an insertion part to take in a magnified observation image of an in vivo mucous membrane with the observation port being in contact with or in close proximity to a surface of the mucous membrane, there is provided a marking means for applying marking liquid to the mucous membrane surface to change a visual appearance state thereof in such a manner as to surround the magnified image observation port.

Embodiments

Figure 1:
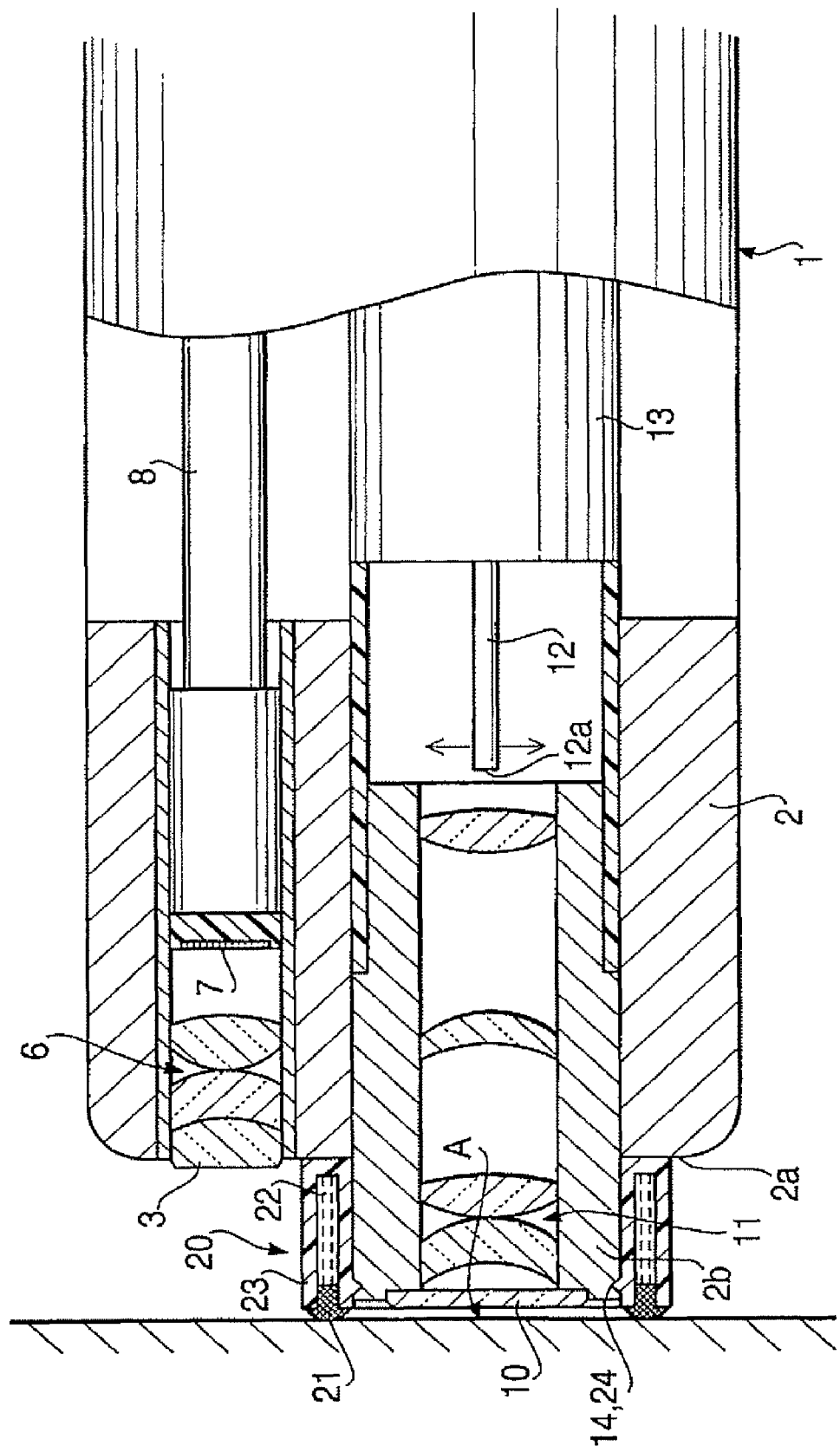
FIG. 1 is a cross-sectional side view of a distal end portion of an insertion part of an endoscope for magnified image observation according to a first embodiment of the present invention.
Figure 2:
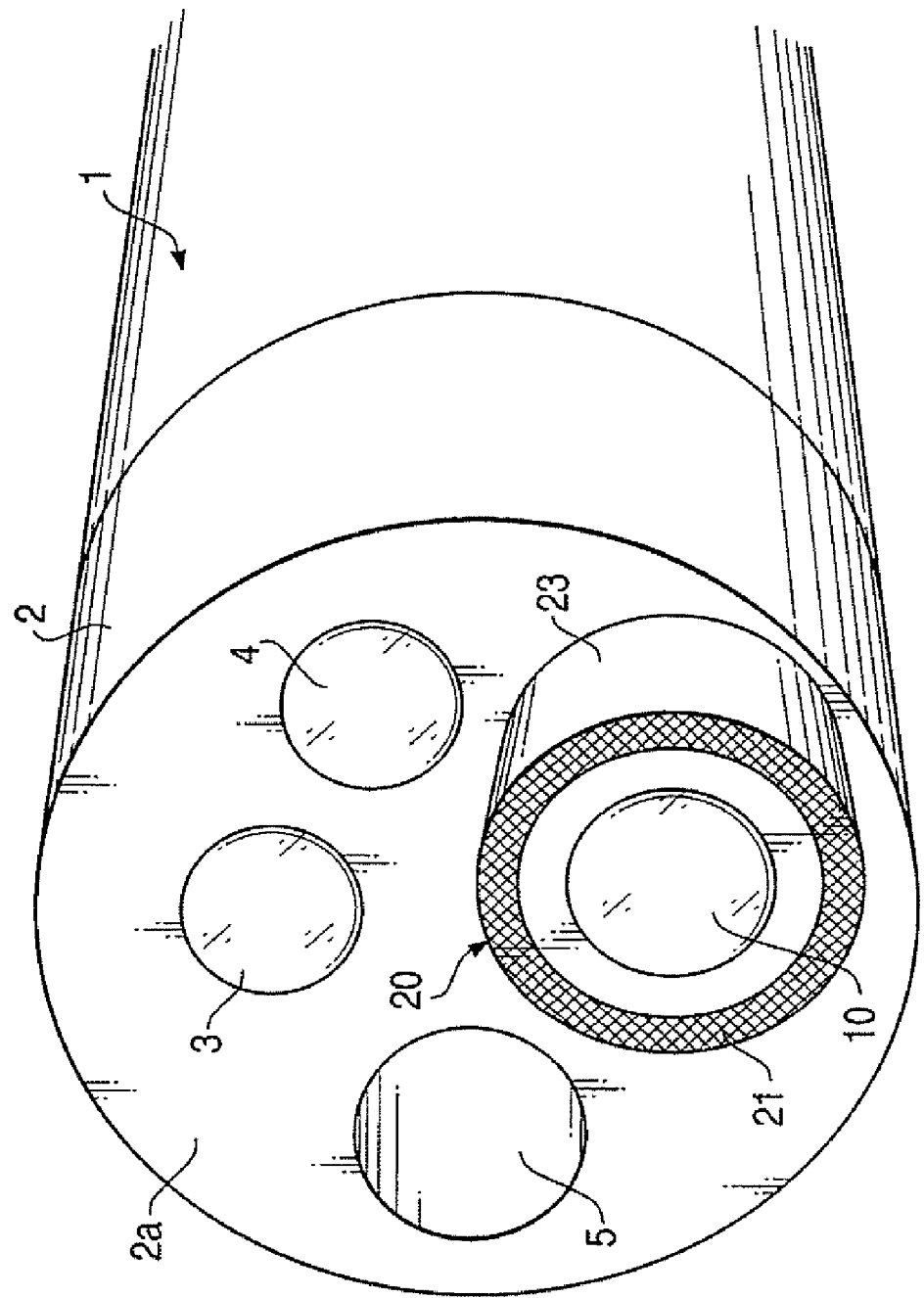
FIG. 2 is a perspective view of the distal end portion of the insertion part of the endoscope for magnified image observation according to the first embodiment of the present invention.

Hereinafter, embodiments of the present invention will be described with reference to the accompanying drawings. FIGS. 1 and 2 show a cross-sectional side view and a perspective view of a distal end portion of an insertion part 1 of an endoscope for magnified image observation in a first embodiment of the present invention, respectively. On a distal end surface 2a of a distal main body portion 2 linked to a leading edge portion of the insertion part 1 formed like a flexible tube, there is arranged an observation port 3 for normal observation, illumination port 4, and treatment tool opening 5. It is noted that an air-and-water-conveying nozzle and the like are not shown in any of the drawings.

In the observation port 3 for normal observation, there is arranged an objective optical system 6 for obtaining a wide viewing angle (e.g., 100~140 degrees). An image sensing surface of a solid-state image sensor 7 is arranged in a position where a subject is projected by the objective optical system 6. What is denoted by a reference sign 8 is a signal cable for transmitting an image sensing signal generated by the solid-state image sensor 7.

On a distal end surface of a protruded portion 2b protruded forward from the distal end surface 2a of the distal main body portion 2, there is arranged an observation port 10 for magnified image observation, directed forward, to take in an observation image of the in vivo mucous membrane with the observation port 10 for magnified image observation being in contact with or in close proximity to the mucous membrane surface as a subject.

Inside the magnified image observation port 10 in the first embodiment, there is arranged a confocal optical system 11, and a single optical fiber 12 that is provided in the back thereof as being two-dimensionally scanned is set such that a location of a distal end surface 12a of the single optical fiber 12 has a confocal positional relationship with a location (or a location slightly ahead) of an outer surface of the magnified image observation port 10.

It is noted that, although the protruded portion 2b, in the first embodiment, is formed with a front portion of a cylindrical barrel supporting the confocal optical system 11 being protruded from the distal end surface 2a of the distal main body portion 2, a portion of the distal main body portion 2 may be protruded forward to form the protruded portion 2b.

The distal end surface 12a of the single optical fiber 12 is two-dimensionally scanned on a plane perpendicular to an optical axis of the confocal optical system 11 by a scanning mechanism 13, for example, using an electromagnetic force. When a laser beam that has been transmitted through the single optical fiber 12 and emitted from the distal end surface 12a is focused and reflected on a subject A in the vicinity of the outer surface of the magnified image observation port 10, the reflected beam is focused on the distal end surface 12a of the single optical fiber 12. It is noted that, when fluorescent dye is applied to the in vivo mucous membrane, fluorescence excited by the laser beam becomes the subject A.

Accordingly, by bringing the reflected beam returned to a rear anchor side through the single optical fiber 12 on a position corresponding to a scanning movement, it is possible to obtain a clear microscopically super-magnified image of an area with a diameter less than 1 mm (e.g., an area with a diameter of 5 mm) of the subject A in the vicinity of the surface of the magnified image observation port 10. It is noted that the optical system in the magnified image observation port 10 may be configured to observe a microscopically super-magnified image without the confocal optical system 11 that uses the distal end surface 12a of the single optical fiber 12 as substitute for a pinhole but with a so-called normal optical system for magnified image observation.

It is a marking unit that changes a visual appearance state of a surface of the in vivo mucous membrane as the subject A with marking liquid being applied thereto that is denoted by a reference sign 20. The marking unit 20 is configured in the form of a cylinder surrounding the protruded portion 2b of the distal main body portion 2 provided with the magnified image observation port 10 on the distal end surface of the protruded portion 2b, and is provided to be detachable from the distal main body portion 2. It is noted that the marking unit 20 will be described with reference to FIGS. 3 and 4 that show a state where the marking unit 20 is detached from the distal main body portion 2.

The marking unit 20 is formed to have (substantially) the same length as a protruded length of the protruded portion 2b from the distal end surface 2a of the distal main body portion 2. At the marking unit 20, there is arranged in the same direction as the magnified image observation port 10 a marking liquid applying member 21 that applies the marking liquid to the in vivo mucous membrane while being in contact therewith in a position of the same level as the outer surface of the magnified image observation port 10 or in a position slightly protruded forward (e.g., by 5 mm) from the outer surface.

The marking liquid applying member 21 is formed as a contiguous ring along an outer edge of the protruded portion 2b (that is, along an outer edge of the magnified image observation port 10) from material such as felt which can absorb the marking liquid well.

A marking liquid filled portion 22 filled with the marking liquid to be supplied to the marking liquid applying member 21 is formed to open forward all around a marking liquid pooling tube 23 formed as a tube surrounding the protruded portion 2b of the distal main body portion 2 in the marking liquid pooling tube 23. A back portion of the marking liquid applying member 21 is tightly fitted and fixed to a distal opening portion of the marking liquid filled portion 22 such that the entire distal opening portion is plugged therewith.

Accordingly, the marking liquid filled into the marking liquid filled portion 22 can always be supplied to the marking liquid applying member 21. It is noted that natural dye such as indigo carmine can be employed as the marking liquid, and that fluorescent dye or magnetic fluid may be employed depending on a post confirming method.

The marking liquid pooling tube 23 is formed from elastically deformable plastic material. A plurality of click protrusions 24 (click members) is formed to be slightly protruded inward from an inner circumferential surface of the marking liquid pooling tube 23, so as to be engaged with and removed from a circumferential groove 14 formed around an outer circumferential surface of the protruded portion 2b of the distal main body portion 2.

Figure 4:
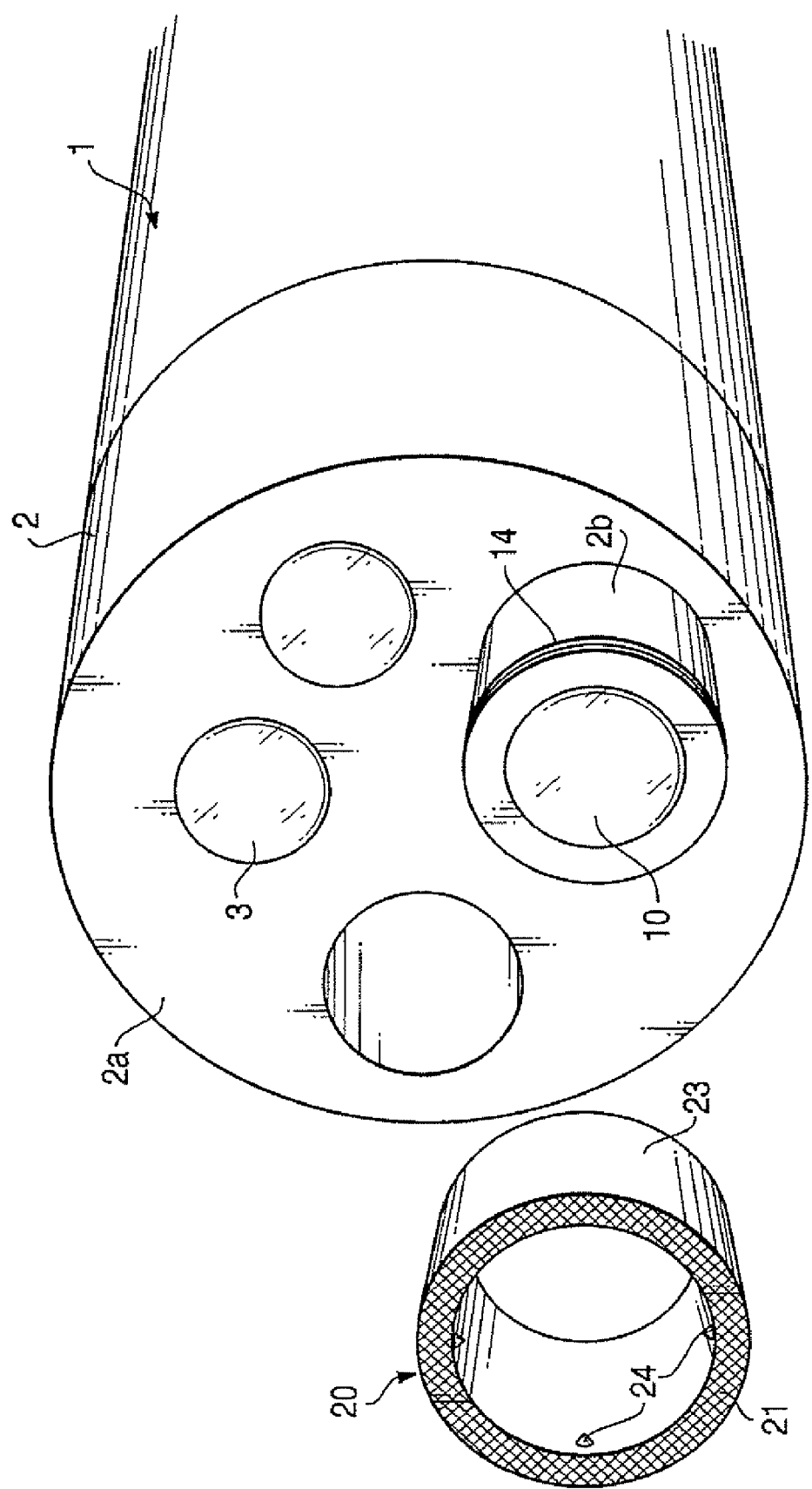
FIG. 4 is a perspective view of the distal end portion of the insertion part of the endoscope for magnified image observation in the state where the marking unit is detached therefrom according to the first embodiment of the present invention.

Consequently, as shown in FIG. 1, in a state where the click protrusions 24 are engaged with the circumferential groove 14, the marking unit 20 is fixed to surround the magnified image observation port 10. It is noted that the fixing is elastically attained by the click protrusions 24. Therefore, when the marking unit 20 is pulled forward with a somewhat large force, as shown in FIGS. 3 and 4, the engagement between the click protrusions 24 and the circumferential groove 14 is disengaged so that the marking unit 20 is removed from the distal main body portion 2.

Figure 5:
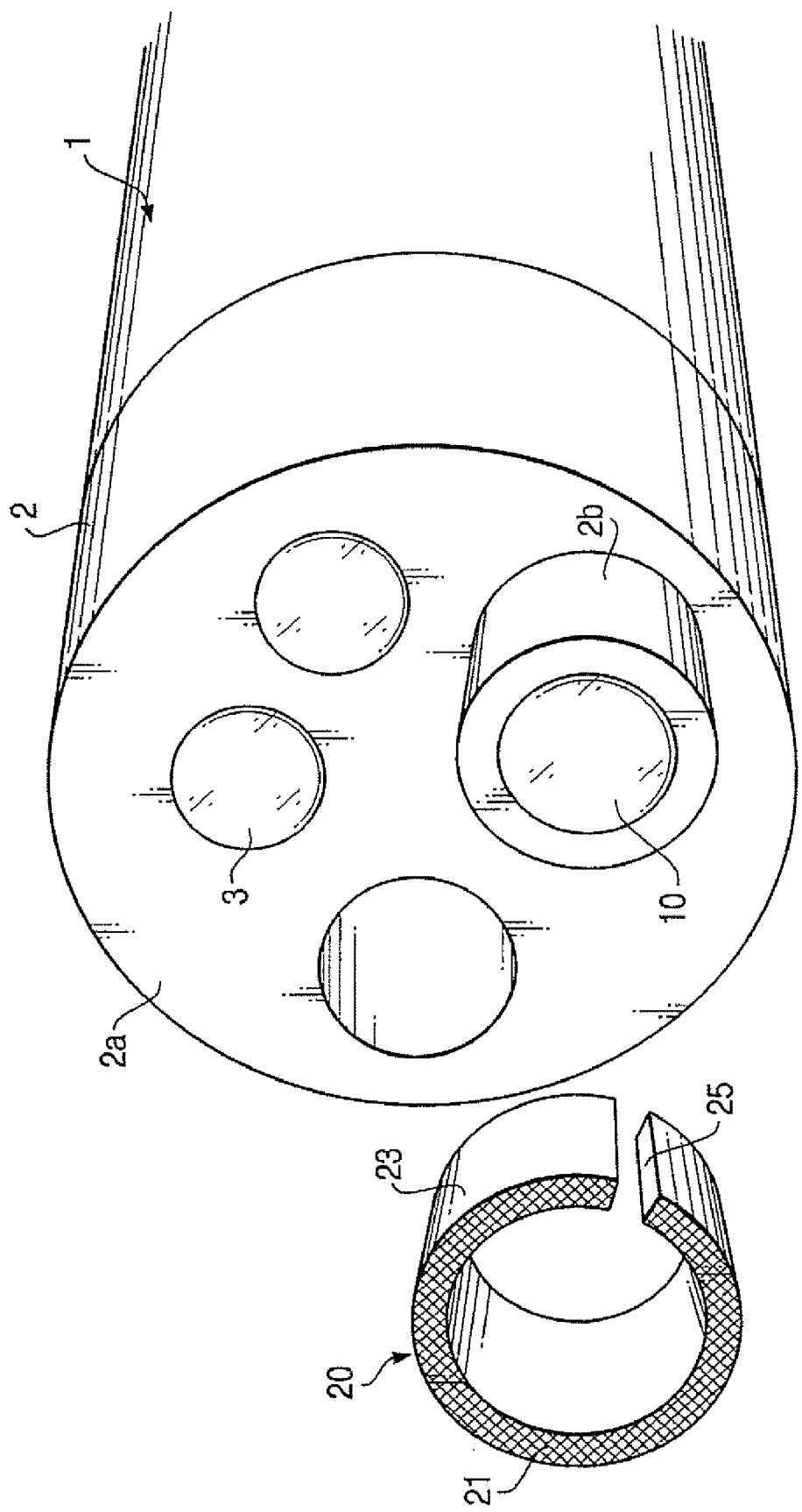
FIG. 5 is a perspective view of the distal end portion of the insertion part of the endoscope for magnified image observation in a state where a marking unit is detached therefrom according to a second embodiment of the present invention.
Figure 6:
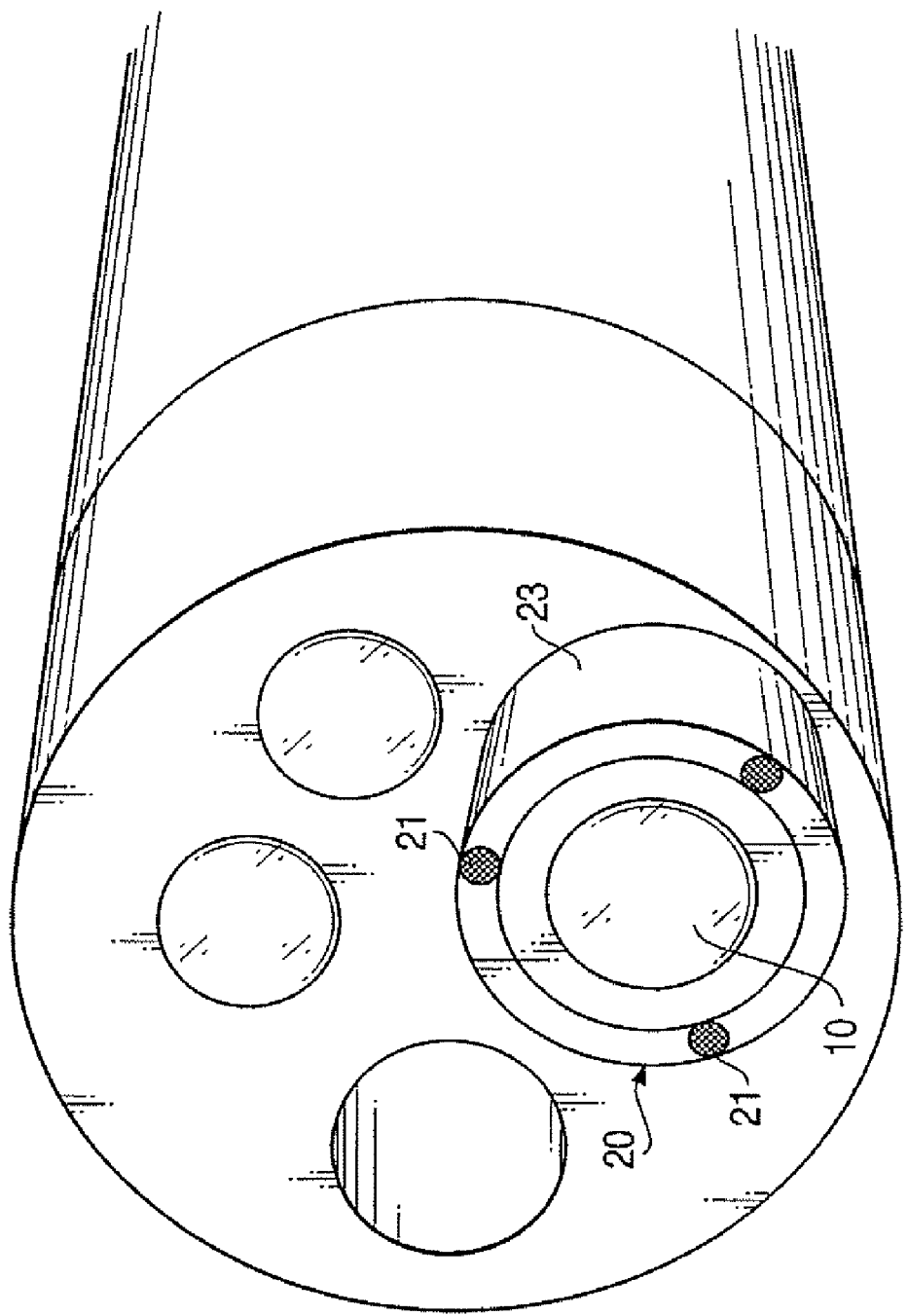
FIG. 6 is a perspective view of the distal end portion of the insertion part of the endoscope for magnified image observation with a marking unit is attached thereto according to a third embodiment of the present invention.

It is noted that various kinds of fixing means for fixing the marking unit 20 to the distal main body portion 2 may be possible. For example, as shown in a second embodiment in FIG. 5, the marking liquid pooling tube 23 may be formed as a noncontiguous ring provided with a slit 25 to have a C-shaped cross-section. In this case, the marking liquid pooling tube 23, being slightly elastically unrolled, can be fitted and fixed to the protruded portion 2b of the distal main body portion 2.

In addition, the marking liquid applying member 21 is not necessarily required to be formed as a ring. For example, as shown in a third embodiment in FIG. 3, it may be formed as a plurality of dots arranged along the outer edge of the magnified image observation port 10 with a space between each adjacent couple of the plurality of dots, or it may be configured to mark a sign, number, or the like.

When using the endoscope for magnified image observation thus configured, a microscopically super-magnified image is observed with the magnified image observation port 10 being in contact with in vivo mucous membrane that has been suspected to be abnormal in an observation image obtained through the observation port 3 for normal observation. Then, it is possible to make a definite diagnosis about whether a cancer cell exists on the spot.

On a surface of the in vivo mucous membrane of which the microscopically super-magnified image is observed with the magnified image observation port 10 being in contact therewith, the marking liquid applying member 21 is pressed in a manner surrounding the observed area to perform the marking operation. As schematically shown in FIGS. 7 and 8, by observing/recording makings 31 in a wide normal observation image 30 through the observation port 3 for normal observation, a location of an area of which the super-magnified image has been observed can very accurately be specified, confirmed, and recorded in the image.

Such an operation of recording the markings 31 may be performed by inserting another endoscope dedicated to normal observation that is separated from the endoscope for magnified image observation. Accordingly, the endoscope for magnified image observation is not necessarily required to have the normal observation function.

FIG. 9 shows a marking unit in a fourth embodiment of the present invention. As shown in FIG. 9, there is provided at a bottom of the marking liquid pooling tube 23 a marking liquid refilling opening 26 for refilling the marking liquid into the marking liquid filled portion 22 of which the marking liquid applying member 21 is fixed to the distal opening portion, and a plug member is detachably attached to the marking liquid refilling opening 26. According to the marking unit 20 thus configured, the entire marking unit 20 can repeatedly be used.

FIG. 10 shows a marking unit 20 in a fifth embodiment of the present invention. As shown in FIG. 10, a marking liquid applying member 21 is configured such that it is capable of being fitted to (that is, detachable from) the distal opening portion of the marking liquid filled portion 22. Further, a sheet 27 for sealing the distal opening portion of the marking liquid filled portion 22 is attached to the marking liquid pooling tube 23. It is a tail portion of the sheet 27 to be grabbed with fingertips that is denoted by a reference sign 27*a*.

According to the marking unit 20 thus configured, when the marking liquid in the marking liquid filled portion 22 is completely used, only the marking liquid applying member 21 is re-used. The marking unit 20 can be used after the sheet 27 is removed from a new marking liquid pooling tube 23 and the marking liquid applying member is attached thereto.

FIG. 11 shows the distal end portion of the insertion part 1 of the endoscope for magnified image observation in a sixth embodiment of the present invention. As shown in FIG. 11, a heretofore known front hood having the marking unit 20, configured to be detachable from the distal end of the distal main body portion 2, is attached to the distal main body portion 2 in a manner surrounding the outer circumferential portion thereof.

A circumferential groove 2*c* is formed on the outer circumferential portion of the distal main body portion 2. An inward protrusion 41 to be engaged with the circumferential groove 2*c* is protruded from an inner circumferential surface of the front hood 40 made from resilient rubber material.

The front food 40 is protruded from the distal end surface 2*a* of the distal main body portion 2 by substantially the same height as the magnified image observation port 10. The same marking unit 20 as that in the first embodiment is formed integrated with the front hood 40. It is noted that the marking unit 20 may be configured to be separatable from the front hood 40.

Consequently, as shown in FIG. 12, when the front hood 40 is attached to or detached from the distal main body portion 2, the marking unit 20 is attached to or detached from the distal main body portion 2 at the same time. Therefore, the attaching/detaching operations become easy.

Further, when the marking liquid in the marking unit 20 is completely used, the marking unit can be exchanged by detaching the front hood 40 from the distal main body portion 2 and exchanging the front hood 40. It is noted that, as shown in a seventh embodiment in FIG. 13, the marking liquid applying member 21 may be formed as dots in the same manner as the third embodiment and may be formed as one of other aspects.

Each of FIGS. 14 to 16 shows a distal end portion of the insertion part 1 of the endoscope for magnified image observation in an eighth embodiment of the present invention. In the eighth embodiment, a marking liquid applying member 21 is formed as a plurality of dots arranged along the outer edge of the magnified image observation port 10 with a space between each adjacent couple of the plurality of dots. The marking unit 20 is provided with a very thin flexible sheet 28 arranged as covering all of the dots 21 to be movable along surfaces thereof. The flexible sheet 28 is configured to be moved by a remote operation from the rear anchor side so as to control the number of the dots to be exposed outside among the plurality of dots.

In the eighth embodiment, with an operating wire 18 coupled to a tail portion 28*a* of the flexible sheet 28 being pulled from the rear anchor side of the insertion part 1, the flexible sheet 28 is gradually drawn into a port 2*d* formed in the distal main body portion 2. As the flexible sheet 28 is drawn, as shown in FIGS. 15 and 16 in sequence, the number of the dots 21 covered with the flexible sheet 28 is reduced, and the number of the dots 21 to be marked on the in vivo mucous membrane is increased.

Thus, by the aforementioned simple configuration for only pulling the operating wire 18 of the flexible sheet 28, the number of the dots to be marked by the marking unit 20 can be controlled from the rear anchor side of the insertion part 1. As schematically shown in FIG. 17, the change of the number of the dots can easily be discriminated in the normal observation image 30, and the location of an area corresponding to each of the super-magnified observation images recorded through the magnified image observation port 10 can be confirmed. It is noted that the marking unit 20 may be configured to change a numerical character or a sign to be used as a marking in sequence instead of changing the number of the dots 21.

The present disclosure relates to the subject matter contained in Japanese Patent Application No. P2005-351954, filed on Dec. 06, 2005, which is expressly incorporated herein by reference in its entirety.

What is claimed is:

1. An endoscope for magnified image observation configured to observe a magnified image of in vivo tissue, comprising:
    an insertion part configured to be inserted into a body;
    a magnified image observation port comprising a confocal optical system, the magnified image observation port being configured to take in the magnified image of the in vivo tissue in a state where the magnified image observation port is in contact with the in vivo tissue, the observation port being provided at a distal end of the insertion part; and
    a marking unit configured to mark the in vivo tissue in the state where the magnified image observation port is in contact with the in vivo tissue,
    the marking unit being configured to mark the in vivo tissue by applying marking liquid to a surface of the in vivo tissue,
    the marking unit comprising a marking liquid pooling tube that surrounds the magnified image observation port,
    the marking unit having a marking liquid applying member provided along an outer edge of the magnified image observation port to apply the marking liquid to the in vivo tissue,
    the marking liquid applying member being formed as a contiguous ring along the outer edge of the magnified image observation port,
    a marking liquid filled portion provided within the marking liquid pooling tube and configured to be filled with the marking liquid to be supplied to the marking liquid applying member, and the marking liquid filled portion being provided adjacent to the marking liquid applying member,
    the marking liquid filled portion having a cylindrical shape and a distal opening that extends continuously all around a front end surface of the marking liquid pooling tube, and a back portion of the marking liquid applying member being inserted within the distal opening such that the distal opening is plugged.

2. The endoscope for magnified image observation according to claim 1, wherein the marking unit is configured to be detachable from the magnified image observation port.

3. The endoscope for magnified image observation according to claim 2, further comprising a fixing mechanism for fixing a state where the marking unit is attached to the magnified image observation port so as to surround the magnified image observation port.

4. The endoscope for magnified image observation according to claim 3, wherein the fixing mechanism is a click member configured to elastically fix the marking unit around the magnified image observation port.

5. The endoscope for magnified image observation according to claim 2, wherein the magnified image observation port is configured to be protruded from a distal end surface of the insertion part, and wherein the marking unit is formed to have the same length as the protruded length of the magnified image observation port.

6. The endoscope for magnified image observation according to claim 1, wherein the marking liquid filled portion is configured such that it is capable of being separated from the marking liquid applying member.

7. The endoscope for magnified image observation according to claim 1, wherein the marking liquid filled portion is integrated with the marking liquid applying member, and wherein the marking unit includes a marking liquid refilling opening for refilling the marking liquid into the marking liquid filled portion.

8. The endoscope for magnified image observation according to claim 1, further comprising a front hood configured to be attached around the distal end of the insertion part so as to surround the distal end of the insertion part, the front hood being configured to be detachable from the distal end of the insertion part, wherein the marking unit is provided at the front hood.

9. The endoscope for magnified image observation according to claim 1, the marking unit further comprising a fixing mechanism having a plurality of protrusions that protrude radially inward from an inner surface of the marking unit, the plurality of protrusions engaging a groove provided in an outer circumferential portion of a protruded portion of the magnified image observation port.

* * * * *